United States Patent
Mitterer et al.

(10) Patent No.: US 10,202,416 B2
(45) Date of Patent: Feb. 12, 2019

(54) PURIFICATION METHOD FOR DIVALENT CATION BINDING PROTEINS ON ANION EXCHANGE RESIN

(75) Inventors: Artur Mitterer, Orth/Donau (AT); Meinhard Hasslacher, Vienna (AT); Christian Fiedler, Vienna (AT)

(73) Assignees: Baxalta Incorporated, Bannockburn (IL); Baxalta GmbH, Zug (CH)

( * ) Notice: Subject to any disclaimer, the term of this patent is extended or adjusted under 35 U.S.C. 154(b) by 65 days.

(21) Appl. No.: 13/098,313

(22) Filed: Apr. 29, 2011

(65) Prior Publication Data
US 2012/0108513 A1 May 3, 2012

Related U.S. Application Data

(60) Provisional application No. 61/329,487, filed on Apr. 29, 2010.

(51) Int. Cl.
*C07K 1/18* (2006.01)
*C07K 14/47* (2006.01)
*C12N 9/64* (2006.01)

(52) U.S. Cl.
CPC ............ *C07K 1/18* (2013.01); *C07K 14/4721* (2013.01); *C12N 9/644* (2013.01); *C12N 9/647* (2013.01); *C12N 9/6437* (2013.01); *C12Y 304/21021* (2013.01); *C12Y 304/21022* (2013.01)

(58) Field of Classification Search
None
See application file for complete search history.

(56) References Cited

U.S. PATENT DOCUMENTS

| | | | |
|---|---|---|---|
| 4,981,952 A | 1/1991 | Yan | |
| 5,633,350 A | 5/1997 | Fischer et al. | |
| 5,714,583 A * | 2/1998 | Foster et al. | 530/384 |
| 6,869,934 B2 | 3/2005 | Mizokami | |
| 2004/0106779 A1* | 6/2004 | Bigler et al. | 530/384 |
| 2008/0207879 A1 | 8/2008 | Mitterer et al. | |
| 2009/0311239 A1 | 12/2009 | Chtourou et al. | |
| 2010/0047428 A1 | 2/2010 | Lejars et al. | |

FOREIGN PATENT DOCUMENTS

| | | |
|---|---|---|
| EP | 0 363 126 A2 | 4/1990 |
| JP | 2009-538884 A | 11/2009 |
| JP | 2009-538885 A | 11/2009 |
| WO | WO 94/05692 A1 | 3/1994 |
| WO | WO 96/40883 A1 | 12/1996 |
| WO | WO 98/35689 A1 | 8/1998 |
| WO | WO 2006/035058 A2 | 4/2006 |
| WO | WO 2006/067230 A1 | 6/2006 |
| WO | WO 2007/026020 A1 | 3/2007 |
| WO | WO 2011/073235 A1 | 6/2011 |
| WO | WO 2011/135071 A1 | 11/2011 |
| WO | WO 2013/053887 A1 | 4/2013 |
| WO | WO 2013/053888 A1 | 4/2013 |

OTHER PUBLICATIONS

Kelly et al ('Robustness testing of a chromatographic purification step used in recombinant factor ix manufacture' in Validation of Biopharmaceutical Manufacturing Processes; ACS Symposium Series, American Chemical Society, Washington DC 1998 pp. 93-113).*
Flairform (retrieved from http://www.flairform.com/hints/conductivity_factors_effecting.htm on Oct. 22, 2014, 1 page).*
Burger, A. et al., "A rapid and efficient purification method for recombinant annexin V for biophysical studies," *FEBS*, Aug. 1993, vol. 329, No. 1, 2, pp. 25-28.
International Search Report dated Jun. 8, 2011, for International Application No. PCT/EP2011/056832 filed on Apr. 29, 2011, 4 pages.
Osborn, E.C., "The Employment of DEAE—Cellulose Columns on a 'Rejection' Principle in the Preparation of Factor VII," *Clinica Chimica Acta*, 1965, vol. 12, pp. 415-418.
Kelley, B.D. et al., "Robustness Testing of a Chromatographic Purification Step Used in Recombinant Factor IX Manufacture," Chapter 8 in *Validation of Biopharmaceutical Manufacturing Processes, ACS Symposium Series 698*, 1998, pp. 93-113.
Josic, D. et al., "Preparation of vitamin K-dependent proteins, such as clotting factors II, VII, IX and X and clotting inhibitor Protein C," *Journal of Chromatography B*, 2003, vol. 790, pp. 183-197.
Harrison, S. et al., "The Manufacturing Process for Recombinant Factor IX," *Seminars in Hematology*, Apr. 1998, vol. 35, No. 2, Suppl 2, pp. 4-10.

\* cited by examiner

*Primary Examiner* — Karlheinz R. Skowronek
*Assistant Examiner* — Ronald T Niebauer
(74) *Attorney, Agent, or Firm* — Morgan, Lewis & Bockius, LLP

(57) ABSTRACT

The present invention relates to a method for the purification of divalent cation binding proteins with high purity on an anion exchange resin material, to divalent cation binding proteins obtainable by said method, and to a kit comprising means for carrying out said method.

8 Claims, 1 Drawing Sheet

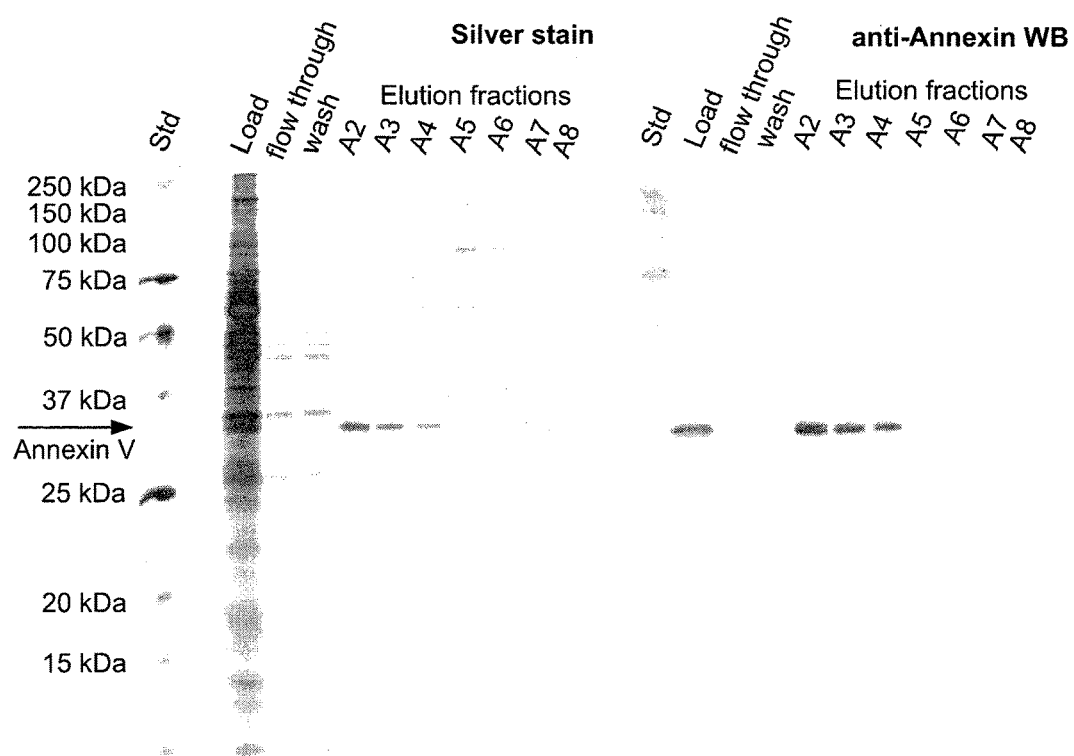

PURIFICATION METHOD FOR DIVALENT CATION BINDING PROTEINS ON ANION EXCHANGE RESIN

CROSS-REFERENCES TO RELATED APPLICATIONS

The present application claims the benefit of U.S. Provisional Application No. 61/329,487, filed Apr. 29, 2010, which is expressly incorporated herein by reference in its entirety for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention relates to a method for the purification of divalent cation binding proteins with high purity on an anion exchange resin material, to divalent cation binding proteins obtainable by said method, and to a kit comprising means for carrying out said method.

BACKGROUND OF THE INVENTION

So far, many mammalian proteins are produced in host tells by e.g., transfecting cells with DNA encoding said proteins and growing the recombinant cells under conditions favorable for the expression of said proteins. The proteins secreted by the cells into the cell culture medium, or residing inside the cells, can be separated from the culture medium and other components using chromatographic techniques, e.g., ion exchange chromatography, affinity chromatography, and the like. For further pharmaceutical applications, purity is of particular importance. However, at the same time the biological activity of the protein must be preserved after thorough purification of the proteins of interest.

The concept of eluting calcium binding proteins from anion exchange resins by divalent cations was firstly reported almost thirty years ago. Although bovine Factor VII was successfully isolated from bovine plasma, the purification of human Factor VII was still problematic, i.e., the material produced was only partially pure or was obtained in such small quantities that it was characterized as activity without detectable protein. Workers in the field succeeded in the isolation of human Factor VII from human plasma in sufficient quantities (with a yield of approx. 30%) by means of adsorbing proteins to a divalent cation, i.e., barium citrate, and then separating the protein by anion exchange chromatography. Further, methods were available for recovering and purifying vitamin K-dependent proteins from the medium of a cell culture producing vitamin K-dependent proteins with different specific activities by means of conventional ion-exchange resins, e.g., anion exchange resins, and using an eluant containing divalent cations, e.g., calcium ion ($Ca^{2+}$), barium ion ($Ba^{2+}$), and strontium ion ($Sr^{2+}$).

Furthermore, methods were available for the purification of Factor IX (FIX) in a solution, comprising the steps of applying the solution containing FIX to an anion exchange resin, washing the anion exchange resin with a solution having a conductivity that is less than required to elute FIX from the resin, and eluting FIX from the anion exchange resin with a first eluant including divalent cations to form a first eluate. The first eluate is then applied to a heparin or heparin-like resin to form a second eluate, and the second eluate is applied to hydroxyapatite to form a third eluate, utilizing a high conductivity washing agent in the washing step.

Factor IX (FIX) is a vitamin K-dependent serine protease of the coagulation system, belonging to the peptidase family S1. FIX is inactive unless activated by Factor XIa or Factor VIIa. For its activation, calcium, membrane phospholipids, and Factor VIII are required. Deficiency of FIX causes the hereditary recessive bleeding disorder hemophilia B, which can be successfully treated by administration of posttranslational modified, i.e., phosphorylated and sulfated FIX.

Further, Factor VII (FVII) is a vitamin K-dependent serine protease which plays a significant role in the coagulation cascade, where it initiates the process of coagulation with tissue factor (TF). Upon vessel injury, TF is exposed to the blood and circulating FVII. Once bound to TF, FVII is activated to FVIIa by thrombin, Factor Xa, IXa, XIIa, and the FVIIa-TF complex whose substrates are FX and FIX. Furthermore, Annexin V is a cellular protein in the annexin group, having the ability to bind in a calcium-dependent manner to phosphatidylserine and to form a membrane-bound two dimensional crystal lattice. It may play a role in blood coagulation, apoptosis, phagocytosis and formation of plasma membrane-derived microparticles.

Thus, the problem underlying the present invention is to provide an improved method for the purification of divalent cation binding proteins with a high purity. The solution to the above technical problem is achieved by the embodiments characterized in the claims.

BRIEF SUMMARY OF THE INVENTION

The present invention relates to a method for the purification of a divalent cation binding protein comprising the steps of: (a) loading an anion exchange resin material with the divalent cation binding protein in a loading buffer in the absence of divalent cations, and optionally washing the loaded anion exchange resin material with a washing buffer in the absence of divalent cations; and (b) eluting the divalent cation binding protein with an eluant comprising at least one divalent cation to form an eluate containing the divalent cation binding protein; wherein the eluant in step (b) has a pH higher than the pH of the washing buffer in step (a), or, in case no washing step is carried out, of the loading buffer in step (a).

Further, the present invention relates to purified divalent cation binding proteins obtainable by the above method, and to a kit comprising means for carrying out the above method.

In one aspect, the present invention provides a method for the purification of a divalent cation binding protein comprising the steps of: (a) loading an anion exchange resin material with the divalent cation binding protein in a loading buffer in the absence of divalent cations; and (b) eluting the divalent cation binding protein with an eluant comprising at least one divalent cation to form an eluate containing the divalent cation binding protein; wherein the eluant in step (b) has a pH higher than the pH of the loading buffer in step (a).

In one embodiment of the methods provided herein, the method further comprises the step of washing the loaded anion exchange resin material prepared in step (a) with a washing buffer in the absence of divalent cations, prior to step (b), wherein the eluant has a higher pH than the pH of the washing buffer. In a specific embodiment, the pH of the eluant in step (b) is at least 0.5 pH units higher than the pH of the washing buffer. In another specific embodiment, the washing buffer has a conductivity that is equal or lower than the conductivity of the eluant in step (b).

In certain embodiments of the methods provided herein, the at least one divalent cation in step (b) is selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, and a combination thereof.

In certain embodiments of the methods provided herein, the anion exchange resin material has a positively charged group which is selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

In certain embodiments of the methods provided herein, the anion exchange resin material carries a primary amine as ligand which is selected from the group, consisting of aminohexyl, benzamidine, lysine, and arginine.

In certain embodiments of the methods provided herein, the divalent cation binding protein is a calcium binding protein.

In certain embodiments of the methods provided herein, the divalent cation binding protein is a vitamin K-dependent protein.

In certain embodiments of the methods provided herein, the divalent cation binding protein is selected from the group, consisting of Factor II, Factor IX, Factor VII, Protein C, ADAMTS13, and Annexin V.

In another aspect, the present invention provides a purified divalent cation binding protein obtainable by any of the purification method described herein.

In one aspect, the present invention provides a pharmaceutical composition of a divalent binding protein prepared according to a method comprising the steps of: (a) contacting a solution comprising the divalent cation binding protein with an anion exchange resin material under a first solution condition lacking available divalent cations at a first pH to bind the protein to the resin; (b) eluting the protein from the resin with a second solution condition comprising available divalent cations at a second pH; and (c) formulating the eluted protein for pharmaceutical administration, wherein the second pH is higher than the first pH.

In one embodiment of the compositions provided herein, the method for preparation further comprises the step of washing the resin formed in step (a), prior to step (b), under a third solution condition lacking available divalent cations at a third pH, wherein the second pH is higher than the third pH.

In one embodiment of the compositions provided herein, the method for preparation further comprises at least one viral inactivation step.

In one embodiment of the compositions provided herein, the divalent cation binding protein is a protein found in the blood of a mammal.

In one embodiment of the compositions provided herein, the protein is a recombinant protein.

In one embodiment of the compositions provided herein, the protein is selected from the group consisting of Factor II, Factor IX, Factor VII, Protein C, ADAMTS13, and Annexin V.

In one embodiment of the compositions provided herein, the protein is selected from the group consisting of Factor IX, Factor VII, and Annexin V.

In one aspect, the resent invention provides a kit comprising means for carrying out a purification method provided herein.

In one embodiment of the kits provided herein, the kit comprises an eluant comprising at least one divalent cation, suitable for eluting a divalent cation binding protein from an anion exchange resin material in a buffer, wherein the eluant has a pH higher than the pH of said buffer.

BRIEF DESCRIPTION OF THE DRAWINGS

FIG. 1: SDS-PAGE of fractions obtained after purification of Annexin V on Q-Sepharose Fast Flow. The SDS-PAGE analysis was carried out on a 12% gel under reducing conditions. The load, column, flow through, wash and elution fractions A2 to A8 were analyzed by a gelelectrophoretic method and the separated polypeptides were visualized by silver staining (total protein stain) or Western blotting using anti-Annexin specific antibodies. Annexin V is a single chain polypeptide with about 36 kDa and can bind up to 10 divalent cation molecules at three different types of binding sites. The position of the Annexin V band is indicated with an arrow.

DETAILED DESCRIPTION OF THE INVENTION

I. Introduction

Among other aspects, the present invention provides efficient methods for the purification of divalent cation binding proteins using an anion exchange resin material allowing a high reduction of process related impurities of the protein with concomitantly high product yields.

In particular, the methods provided herein are based on the following principles. Generally, binding of proteins to anion exchange resin materials is increased at lower conductivities and higher pH values. Vice versa, binding of proteins to anion exchange resin materials is decreased at higher conductivities and lower pH values. In the method of the present invention, the divalent cation binding protein is preferably loaded and/or washed at a low pH which still allows binding of the divalent cation binding protein to the anion exchange material and does not harm the structural integrity or the activity of the divalent cation binding protein. At such conditions, many protein impurities, in particular those having a higher isoelectric point (pI) than the divalent cation binding proteins, do not bind to the anion exchange resin material, and, therefore, binding of impurities to the anion exchange resin material is greatly reduced. Protein impurities that do bind to the anion exchange resin material under these conditions, i.e., protein impurities having a low pI, will not coelute with the divalent cation binding protein since the increase of the pH in the elution buffer causes all proteins, including the divalent cation binding protein, to bind even stronger to the anion exchange resin material. According to the method of the present invention, only the divalent cation binding protein is specifically eluted under such elution conditions due to the divalent cations present in the elution buffer. In this context, it should be noted that elution from an anion exchange resin material at increased pH values is very atypical, since, as has been stated above, proteins generally bind stronger to anion exchange resin materials at higher pH values. By specifically eluting the divalent cation binding proteins with an eluant comprising at least one divalent cation under the above conditions, the method of the present invention surprisingly and advantageously achieves superior purities of the divalent cation binding protein product with a single purification step by anion exchange chromatography.

In particular, the present invention advantageously modifies the surface charge of the proteins to be purified by increasing the pH between the loading step and/or the washing step of step (a) of the method of the present invention, and the step of eluting the divalent cation binding protein. An increased pH in the elution step forces impurities to remain adsorbed to the anion exchange resin material while specific elution of the protein to be purified with divalent cations at a high pH is carried out. In particular, a high pH is normally an unfavorable condition for driving elution from an anion exchange resin material, since proteins bind stronger to an anion exchange resin material at higher pH values. However, according to the present invention, the above conditions result in a high purity as well as high yields of divalent cation binding proteins. The method of the present invention may provide a significant reduction of process related polypeptide impurities e.g., by loading the protein solution at neutral pH onto an anion exchange resin material, applying a wash step at reduced pH, and eluting the product at an increased pH in the presence of a divalent cation. Instead of the low pH wash the sample can already be loaded at a low pH followed by elution at increased pH in the presence of a divalent cation.

II. Definitions

As used herein, the term "anion exchange resin material" does not underlie a specific restriction. According to the present invention, the resin includes any material suitable for anion exchange chromatography known in the art, for example an agarose based chromatography material, e.g., sepharoses for example Fast Flow or Capto, polymeric synthetic material, e.g., polymethacrylate for example Toyopearls, polystyrene/divinylbenzene, e.g., Poros, Source, or cellulose, e.g., Cellufine. In a specific example of the present invention, the anion exchange resin material is sepharose, which is based on modified agarose, the polysaccharide chains of which are crosslinked to form a three-dimensional network. In a preferred embodiment, the anion exchange resin material includes, but is not limited to a resin that carries a primary amine as ligand, e.g., aminohexyl sepharose, benzamidine sepharose, lysine sepharose, or arginine sepharose. In another preferred embodiment, the anion exchange resin material includes, but is not limited to a resin having a positively charged moiety at neutral pH, such as alkylaminoethane, for example diethylaminoethane (DEAE), dimethylaminoethane (DMAE), or trimethylaminoethyl (TMAE), polyethyleneimine (PEI), quaternary aminoalkyl, quaternary aminoethane (QAE), quaternary ammonium (Q), and the like. In a particularly preferred embodiment the anion exchange resin material is Q-Sepharose Fast Flow (Q-Sepharose FF).

The term "impurity" as used herein includes any impurity originating from the production of the divalent cation binding protein and may include e.g., host cell protein impurities, nucleic acid impurities, polypeptide impurities, buffer and salt impurities, impurities originating from the cell culture medium, product related impurities, such as dimers or fragments, and combinations thereof.

As used herein, the phrases "in the absence of divalent cations" or "lacking available divalent cations" can be used interchangeably and refer to a solution state in which either substantially no divalent cations are present or substantially all of the divalent cations are chelated by a suitable chelation agent, e.g., EDTA or EGTA. Accordingly, divalent cations free in solution and protein-bound divalent cations may only be present at insignificant levels or substantially undetectable levels, however, divalent cations that are complexed with or by a chelator, e.g., EDTA or EGTA, may be present.

III. Purification Methods

In one aspect, the present invention relates to a method for the purification of a divalent cation binding protein comprising the steps of: (a) loading an anion exchange resin material with the divalent cation binding protein in a loading buffer in the absence of divalent cations, and optionally washing the loaded anion exchange resin material with a washing buffer in the absence of divalent cations; and (b) eluting the divalent cation binding protein with an eluant comprising at least one divalent cation to form an eluate containing the divalent cation binding protein; wherein the eluant in step (b) has a pH higher than the pH of the washing buffer in step (a), or, in case no washing step is carried out, of the loading buffer in step (a).

Loading of the anion exchange resin material with the divalent cation binding protein in a loading buffer in the absence of divalent cations can be carried out by any method known in the art. In particular, conditions suitable for loading the divalent cation binding protein to the anion exchange resin material are well known to a person skilled in the art. The specific conditions for the conductivity of the loading buffer that allows binding of the product depend on the particular properties of the protein and the anion exchange resin material used (e.g., ligand density, ligand presentation, etc.). Divalent cations bind to proteins in regions that are usually highly acidic (i.e., negatively charged). The negative charges are masked when the divalent cation is bound. However, by loading the anion exchange material with the divalent cation binding protein in the absence of divalent cations, e.g., by stripping off the bound divalent cation by a chelator, e.g., EDTA, the protein carries highly negatively charged patches on the surface that allow strong binding to an anion exchange ligand. The conditions for loading a protein onto an anion exchange resin material further always require a balance between pH and the concentration of the counterions, e.g., $Cl^-$. The chemistry of the counterion also influences the elution behavior, e.g., $Cl^-$ carries one negative charge, and phosphate at neutral pH carries two negative charges. The latter can have a higher eluting power compared to $Cl^-$, even when the conductivity is lower.

The salt concentrations of the solutions and buffers used in the present invention are typically in the range between 20 and 200 mM, preferably between 100 and 150 mM.

Further, suitable loading buffers for loading a divalent cation binding protein to an anion exchange material in step (a) of the method of the present invention, providing conditions under which the divalent cation binding protein is bound to the anion exchange material are well known in the art. For example, the loading buffer can have a pH <pH 7.4, preferably <pH 7.0, more preferably <pH 6.5, and most preferably <pH 6.0. It may contain any salt concentrations suitable for binding the divalent cation binding protein to the anion exchange resin material which may be easily determined by a person skilled in the art. In a preferred embodiment, the loading buffer may contain a chelating agent, e.g., EDTA, preferably 2 mM EDTA. A loading buffer containing the divalent cation binding protein which may be applied to the anion exchange resin material in the method of the present invention may contain, for example, 20 mM Tris, 150 mM NaCl, and 2 mM EDTA.

In one embodiment of the methods provided herein, the salt concentration of the first solution condition (i.e., the loading buffer) is between about 20 mM and about 500 mM. In another embodiment, the salt concentration is between about 20 mM and about 400 mM. In another embodiment, the salt concentration is between about 20 mM and about 300 mM. In yet another embodiment, the salt concentration is between about 20 mM and about 200 mM. In certain embodiments, the salt concentration of the first solution condition (i.e., the loading buffer) is about 20 mM, or about 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, or higher.

In one embodiment of the methods provided herein, the pH of the first solution condition (i.e., the loading buffer) is less than about 9.0. In another embodiment, the pH is less than about 8.5. In another embodiment, the pH is less than about 8.0. In another embodiment, the pH is less than about 7.5. In another embodiment, the pH is less than about 7.0. In another embodiment, the pH is less than about 6.5. In another embodiment, the pH is less than about 6.0. In yet other embodiments, the pH of the first solution condition (i.e., the loading buffer) is less than about 9.0, or less than about 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, or lower.

The method of the present invention optionally comprises the step of washing the loaded anion exchange resin material with a washing buffer in the absence of divalent cations. This washing step can be carried out by any method known in the art. Suitable washing buffers for washing impurities off the anion exchange material essentially without eluting the divalent cation binding protein are well known in the art. For example, the washing buffer can have a pH <pH 7.4, preferably <pH 7.0, more preferably <pH 6.5, and most preferably <pH 6.0. It may contain any salt concentrations suitable for washing the anion exchange resin material without eluting the divalent cation binding protein in a significant amount which may be easily determined by a person skilled in the art. For example, the washing buffer may contain a suitable buffer agent for example Tris or MES, preferably 20 mM Tris or 20 mM MES. Additionally, it may contain a chelating agent for example EDTA, preferably 2 mM EDTA. Further, it may contain a suitable salt for regulating the conductivity of the washing buffer, for example NaCl, which may be present in a concentration of <200 mM, preferably from 100 mM to 200 mM, more preferably from 150 mM to 200 mM, more preferably from 170 mM to 190 mM, and most preferably from 175 mM to 185 mM. In another preferred embodiment of the present application, the washing buffer contains 100 to 200 mM NaCl. The absolute value for the salt concentration depends on the divalent cation binding protein to be purified, wherein it is within the knowledge of the person skilled in the art to determine which divalent cation binding proteins require lower or higher salt concentrations to get the optimal purity.

In one embodiment of the methods provided herein, the salt concentration of the third solution condition (i.e., the wash buffer) is between about 20 mM and about 500 mM. In another embodiment, the salt concentration is between about 20 mM and about 400 mM. In another embodiment, the salt concentration is between about 20 mM and about 300 mM. In yet another embodiment, the salt concentration is between about 20 mM and about 200 mM. In certain embodiments, the salt concentration of the third solution condition (i.e., the wash buffer) is about 20 mM, or about 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, or higher.

In one embodiment of the methods provided herein, the pH of the third solution condition (i.e., the wash buffer) is less than about 9.0. In another embodiment, the pH is less than about 8.5. In another embodiment, the pH is less than about 8.0. In another embodiment, the pH is less than about 7.5. In another embodiment, the pH is less than about 7.0. In another embodiment, the pH is less than about 6.5. In another embodiment, the pH is less than about 6.0. In yet other embodiments, the pH of the third solution condition (i.e., the wash buffer) is less than about 9.0, or less than about 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, or lower.

Additionally, the method of the present invention may further comprise at least one additional washing step after step (a) and before step (b), wherein the conductivity of the additional washing buffer is equal or lower than the conductivity of the eluant. This additional washing step is carried out in the absence of divalent cations. In one embodiment, the additional washing buffer has a pH of 7.4. The additional washing buffer may contain any suitable salt concentration known to a person skilled in the art. Further, the additional washing buffer may contain a buffering agent for example Tris, preferably 20 mM Tris, HEPES, Tris/acetate, Histidine, Gly-Gly, MOPS, or Tricine at typical concentrations of 5 to 50 mM and may contain a counterion, e.g. at a concentration that provides a lower conductivity than the elution buffer. In a preferred embodiment of the present invention, the additional washing buffer has a lower salt concentration than the eluant. In another preferred embodiment, the additional washing buffer contains a chelating agent for example EDTA, preferably 2 mM EDTA.

Eluting the divalent cation binding protein with an eluant comprising at least one divalent cation to form an eluate containing the divalent cation binding protein can be carried out by any method known in the art. However, according to the present invention, the eluant in step (b) has a pH higher than the pH of the washing buffer in step (a), or, in case no washing step is carried out, of the loading buffer in step (a). Preferably, the eluant has a pH≥7.4, more preferably ≥8.0, and the washing buffer in step (a), or, in case no washing step is carried out, the loading buffer in step (a) has a pH of ≤7.4, more preferably ≤7.0, more preferably ≤6.5, and most preferably ≤6.0, provided the pH of the eluant in step (b) is higher than the pH of the washing buffer in step (a), or, in case no washing step is carried out, of the loading buffer in step (a). In a preferred embodiment, the pH of the eluant in step (b) is at least 0.5 pH units, preferably 1.0 pH units, more preferably at least 1.5 pH units, most preferably at least 2.0 pH units higher than the pH of the washing buffer in step (a), or, in case no washing step is carried out, of the loading buffer in step (a).

In one embodiment of the methods provided herein, the pH of the second solution condition (i.e., the elution buffer) is higher than about 9.0. In another embodiment, the pH is higher than about 8.5. In another embodiment, the pH is higher than about 8.0. In another embodiment, the pH is higher than about 7.5. In another embodiment, the pH is higher than about 7.0. In another embodiment, the pH is higher than about 6.5. In another embodiment, the pH is higher than about 6.0. In yet other embodiments, the pH of the second solution condition (i.e., the elution buffer) is higher than about 9.0, or higher than about 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, or lower.

As used herein, the eluant may contain any salt concentrations suitable for eluting the divalent cation binding protein from the anion exchange resin material without eluting impurities in a significant amount which may be easily determined by a person skilled in the art. For example, it may contain a suitable buffer agent, for example, Tris, preferably 20 mM Tris, HEPES, Tris/acetate, histidine, Gly-Gly, MOPS, or tricine, at concentrations ranging typically from 5 to 50 mM. It may also contain a suitable salt for regulating the conductivity of the washing buffer, for example NaCl, which may be present in a concentration of >150 mM, more preferably >180 mM, and most preferably >195 mM. In a preferred embodiment of the present invention, the conductivity of all buffers used in the method of the present invention is about the same. In another preferred embodiment, the washing buffer in step (a), or, in case no washing step is carried out, the loading buffer in step (a) has a conductivity that is equal or lower than the conductivity of the eluant in step (b).

In one embodiment of the methods provided herein, the salt concentration of the second solution condition (i.e., the elution buffer) is between about 20 mM and about 500 mM. In another embodiment, the salt concentration is between about 20 mM and about 400 mM. In another embodiment, the salt concentration is between about 20 mM and about 300 mM. In yet another embodiment, the salt concentration is between about 20 mM and about 200 mM. In certain embodiments, the salt concentration of the second solution condition (i.e., the elution buffer) is at least 20 mM, or about 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, or higher.

The eluant according to the present invention further contains at least one divalent cation. In a preferred embodiment, the eluant comprises a divalent cation, selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, or combinations thereof. The cation is preferably present in the eluant in a concentration from 1 mM to 20 mM, more preferably in a concentration of 2 mM. The cation is present in the eluant in the form of a suitable salt with an anion. Suitable anions are known to a person skilled in the art and comprise for example sulfate-, phosphate-, carbonate-, and borate-based anions, or combinations thereof. The salt comprising the divalent cation may be present in the eluant in a concentration from 1 mM to 20 mM, preferably 2 mM. In a preferred embodiment, the salt is $CaCl_2$. In a particularly preferred embodiment, the eluant contains 2 mM $CaCl_2$. In further preferred embodiments, the eluant contains 2 mM $Ca^{2+}$ and has a pH that is at least 0.5 pH units, preferably at least 1.0 pH units, more preferably at least 1.5 pH units, most preferably at least 2.0 pH units higher than the pH of the washing buffer in step (a), or, in case no washing step is carried out, of the loading buffer in step (a).

The divalent cation binding protein according to the present invention may be any divalent cation binding protein, for example a calcium binding protein and/or a vitamin K-dependent protein. In a preferred embodiment, the divalent cation binding protein is selected from the group, consisting of Factor II, Factor IX, Factor VII, Protein C, ADAMTS13, and Annexin V.

The divalent cation binding protein may be obtained using methods known to a person skilled in the art, e.g., plasma derived proteins, transgenically produced proteins, or recombinantly produced proteins, for example using CHO cells. Secretory and non-secretory methods for extracting proteins from cell culture are well known to a person skilled in the art. This may include any method known in the art for (i) the production of recombinant DNA by genetic engineering, e.g., via reverse transcription of RNA and/or amplification of DNA, (ii) the introduction of recombinant DNA into prokaryotic or eukaryotic cells by transfection, e.g., via electroporation or microinjection, (iii) the cultivation of said transformed cells, e.g., in a continuous or batchwise manner, (iv) the expression of a divalent cation binding protein, e.g., constitutive or upon induction, and (v) the isolation of the protein, e.g., from the culture medium or by harvesting the transformed cells, in order to obtain a crude divalent cation binding protein. Additionally, the recombinant DNA encoding a divalent cation binding protein, e.g., a plasmid, may also contain a DNA sequence encoding a selectable marker for selecting the cells which have been successfully transfected with the recombinant DNA.

The proteins may be further purified, either prior to or after the anion exchange steps described herein, to reduce impurities, for example by gel electrophoresis, chromatography, gel filtration, centrifugation, filtration, precipitation, crystallization or any other method known in the art.

In a preferred embodiment, the divalent cation binding protein which has been purified according to the method of the present invention has a purity with respect to host cell protein impurities of at least 95% w/w, more preferably at least 98% w/w, more preferably at least 99% w/w, and most preferably at least 99.5% w/w divalent cation binding protein in total protein. Accordingly, in a preferred embodiment, the content of impurities in the purified divalent cation binding protein is less than 5% w/w, more preferably less than 2% w/w, more preferably less than 1% w/w, and most preferably less than 0.5% w/w. The percentage values of the impurities refer to w/w of product, i.e., the purified divalent cation binding protein, and can be measured, for example, by HPLC or ELISA.

In one aspect, the present invention provides a method for purifying a divalent cation binding protein, comprising the steps of: (a) contacting a solution comprising a divalent cation binding protein with an anion exchange resin material under a first solution condition lacking available divalent cations at a first pH to bind the protein to the resin; and (b) eluting the protein from the resin with a second solution condition comprising available divalent cations at a second pH, wherein the second pH is higher than the first pH.

In one embodiment, the method further comprises the step of washing the resin formed in step (a), prior to step (b), under a third solution condition lacking available divalent cations at a third pH, wherein the second pH is higher than the third pH.

In one embodiment of the methods provided herein, the pH of the elution buffer (i.e., the second pH) is at least 0.5 pH units higher than the pH of the loading buffer (i.e., the first pH). In another embodiment, the pH of the elution buffer (i.e., the second pH) is at least 1.0 pH units higher than the pH of the loading buffer (i.e., the first pH). In yet other embodiments, the pH of the elution buffer (i.e., the second pH) is at least 0.1 pH units higher or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units higher than the pH of the pH of the loading buffer.

In one embodiment of the methods provided herein, the pH of the elution buffer (i.e., the second pH) is at least 0.5 pH units higher than the pH of the wash buffer (i.e., the third pH). In another embodiment, the pH of the elution buffer (i.e., the second pH) is at least 1.0 pH units higher than the pH of the wash buffer (i.e., the third pH). In yet other embodiments, the pH of the elution buffer (i.e., the second pH) is at least 0.1 pH units higher or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units higher than the pH of the wash buffer.

In one embodiment of the methods provided herein, the pH of the wash buffer (i.e., the third pH) is the same as the pH of the loading buffer (i.e., the first pH).

In another embodiment, the pH of the wash buffer (i.e., the third pH) is lower than the pH of the loading buffer (i.e., the first pH). In one embodiment, the pH of the wash buffer (i.e., the third pH) is at least 0.5 pH units lower than the pH of the loading buffer (i.e., the first pH). In another embodiment, the pH of the wash buffer (i.e., the third pH) is at least 1.0 pH units lower than the pH of the loading buffer (i.e., the first pH). In yet other embodiments, the pH of the wash buffer (i.e., the third pH) is at least 0.1 pH units lower or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units lower than the pH of the loading buffer.

In another embodiment, the pH of the wash buffer (i.e., the third pH) is higher than the pH of the loading buffer (i.e., the first pH). In one embodiment, the pH of the wash buffer (i.e., the third pH) is at least 0.5 pH units higher than the pH of the loading buffer (i.e., the first pH). In another embodiment, the pH of the wash buffer (i.e., the third pH) is at least 1.0 pH units higher than the pH of the loading buffer (i.e., the first pH). In yet other embodiments, the pH of the wash buffer (i.e., the third pH) is at least 0.1 pH units higher or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units higher than the pH of the loading buffer.

In one embodiment of the methods provided herein, the conductivity of the elution buffer is equal to or less than the conductivity of the loading buffer. In one embodiment, the conductivity of the elution buffer is at least 0.5 mS/cm lower than the conductivity of the loading buffer. In another embodiment, the conductivity of the elution buffer is at least 1.0 mS/cm lower than the conductivity of the loading buffer. In yet other embodiments, the conductivity of the elution buffer is at least 0.1 mS/cm lower or at least 0.2, 0.3, 0.4, 0.5, 0.6, 0.7, 0.8, 0.9, 1.0, 1.5, 2.0, 2.5, 3.0, 3.5, 4.0, 4.5, 5.0, or more lower than the conductivity of the loading buffer.

In another embodiment of the methods provided herein, the conductivity of the elution buffer is equal to or less than the conductivity of the wash buffer. In one embodiment, the conductivity of the elution buffer is at least 0.5 mS/cm lower than the conductivity of the wash buffer. In another embodiment, the conductivity of the elution buffer is at least 1.0 mS/cm lower than the conductivity of the wash buffer. In yet other embodiments, the conductivity of the elution buffer is at least 0.1 mS/cm lower or at least 0.2, 0.3, 0.4, 0.5, 0.6, 0.7, 0.8, 0.9, 1.0, 1.5, 2.0, 2.5, 3.0, 3.5, 4.0, 4.5, 5.0, or more lower than the conductivity of the wash buffer.

In one embodiment of the methods provided herein, the divalent cation present in the elution buffer is selected from the group consisting of Ca2+, Be2+, Ba2+, Mg2+, Mn2+, Sr2+, Zn2+, Co2+, Ni2+, and Cu2+, and a combination thereof.

In one embodiment of the methods provided herein, the concentration of divalent cation present in the second solution condition (i.e., the elution buffer) is between about 0.1 mM and about 20 mM. In another embodiment, the concentration of divalent cation present in the elution buffer is between about 0.5 mM and about 10 mM. In another embodiment, the concentration of divalent cation present in the elution buffer is between about 1 mM and about 5 mM. In another embodiment, the concentration of divalent cation present in the elution buffer is between about 1 mM and about 3 mM. In another embodiment, the concentration of divalent cation present in the elution buffer is between about 1 mM and about 2 mM. In a specific embodiment, the concentration of the divalent cation present in the elution buffer is about 0.5 mM. In another embodiment, the concentration of divalent cation present in the elution buffer is about 1.0. In another embodiment, the concentration of divalent cation present in the elution buffer is about 2.0. In yet other embodiments, the concentration of divalent cation present in the elution buffer is about 0.1 mM or about 0.2 mM, 0.3 mM, 0.4 mM, 0.5 mM, 0.6 mM, 0.7 mM, 0.8 mM, 0.9 mM, 1.0 mM, 1.5 mM, 2.0 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 11 mM, 12 mM, 13 mM, 14 mM, 15 mM, 16 mM, 17 mM, 18 mM, 19 mM, 20 mM, 25 mM, 30 mM, or more.

In one embodiment of the methods provided herein, the anion exchange resin material has a positively charged group which is selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

In one embodiment of the methods provided herein, the anion exchange resin material has a positively charged group which is selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

In one embodiment of the methods provided herein, the anion exchange resin material carries a primary amine as ligand which is selected from the group, consisting of aminohexyl, benzamidine, lysine, and arginine.

In one embodiment of the methods provided herein, the divalent cation binding protein is a calcium binding protein. In one embodiment, the divalent cation binding protein is a protein found in blood. In one embodiment, the protein is a plasma-derived protein. In another embodiment, the protein found in blood is recombinantly expressed. In a specific embodiment, the divalent cation binding protein is selected from the group consisting of Factor IX, Factor VII, Annexin V, Factor X, Protein C, and an ADAMTS protease (e.g., ADAMTS13). In one embodiment, the calcium binding protein contains a GLA domain. In a specific embodiment, the GLA domain containing protein is selected from BGLAP; FX; FII; FVII; FIX; GAS6; MGP; PROC; PROS1; PROZ; PRRG1; PRRG2; PRRG3; and PRRG4.

In one embodiment, the divalent cation binding protein is a vitamin K-dependent protein. In one embodiment, the vitamin K-dependent protein is plasma-derived. In another embodiment, the vitamin K-dependent protein is recombinant. In a specific embodiment, the divalent cation binding protein is selected from the group, consisting of Factor IX, Factor VII, and Annexin V.

The present invention further relates to the use of the method of the present invention as defined above and/or of the kit of the present invention as defined above for the purification of a divalent cation binding protein.

IV. Divalent Cation Binding Proteins

Further, in another aspect of the present invention, a purified divalent cation binding protein is provided which is obtainable by the method of the present invention.

In one embodiment, the present invention provides a composition comprising a divalent cation binding protein prepared by a method comprising the steps of (a) loading an anion exchange resin material with the divalent cation binding protein in a loading buffer in the absence of divalent cations, and optionally washing the loaded anion exchange resin material with a washing buffer in the absence of divalent cations; and (b) eluting the divalent cation binding protein with an eluant comprising at least one divalent cation to form an eluate containing the divalent cation binding protein; wherein the eluant in step (b) has a pH higher than the pH of the washing buffer in step (a), or, in case no washing step is carried out, of the loading buffer in step (a).

In another embodiment, the present invention provides a composition comprising a divalent cation binding protein prepared by a method comprising the steps of: (a) contacting a solution comprising the divalent cation binding protein with an anion exchange resin material under a first solution condition lacking available divalent cations at a first pH to bind the protein to the resin; and (b) eluting the protein from the resin with a second solution condition comprising available divalent cations at a second pH, wherein the second pH is higher than the first pH.

In one embodiment, the method further comprises the step of washing the resin formed in step (a), prior to step (b), under a third solution condition lacking available divalent cations at a third pH, wherein the second pH is higher than the third pH.

In one embodiment, the pH of the elution buffer (i.e., the second pH) is at least 0.5 pH units higher than the pH of the loading buffer (i.e., the first pH). In another embodiment, the pH of the elution buffer (i.e., the second pH) is at least 1.0 pH units higher than the pH of the loading buffer (i.e., the first pH). In yet other embodiments, the pH of the elution buffer (i.e., the second pH) is at least 0.1 pH units higher or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units higher than the pH of the pH of the loading buffer.

In one embodiment, the pH of the elution buffer (i.e., the second pH) is at least 0.5 pH units higher than the pH of the wash buffer (i.e., the third pH). In another embodiment, the pH of the elution buffer (i.e., the second pH) is at least 1.0 pH units higher than the pH of the wash buffer (i.e., the third pH). In yet other embodiments, the pH of the elution buffer (i.e., the second pH) is at least 0.1 pH units higher or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units higher than the pH of the wash buffer.

In one embodiment, the pH of the wash buffer (i.e., the third pH) is the same as the pH of the loading buffer (i.e., the first pH).

In another embodiment, the pH of the wash buffer (i.e., the third pH) is lower than the pH of the loading buffer (i.e., the first pH). In one embodiment, the pH of the wash buffer (i.e., the third pH) is at least 0.5 pH units lower than the pH of the loading buffer (i.e., the first pH). In another embodiment, the pH of the wash buffer (i.e., the third pH) is at least 1.0 pH units lower than the pH of the loading buffer (i.e., the first pH). In yet other embodiments, the pH of the wash buffer (i.e., the third pH) is at least 0.1 pH units lower or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units lower than the pH of the loading buffer.

In another embodiment, the pH of the wash buffer (i.e., the third pH) is higher than the pH of the loading buffer (i.e., the first pH). In one embodiment, the pH of the wash buffer (i.e., the third pH) is at least 0.5 pH units higher than the pH of the loading buffer (i.e., the first pH). In another embodiment, the pH of the wash buffer (i.e., the third pH) is at least 1.0 pH units higher than the pH of the loading buffer (i.e., the first pH). In yet other embodiments, the pH of the wash buffer (i.e., the third pH) is at least 0.1 pH units higher or at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more pH units higher than the pH of the loading buffer.

In one embodiment, the conductivity of the elution buffer is equal to or less than the conductivity of the loading buffer. In one embodiment, the conductivity of the elution buffer is at least 0.5 mS/cm lower than the conductivity of the loading buffer. In another embodiment, the conductivity of the elution buffer is at least 1.0 mS/cm lower than the conductivity of the loading buffer. In yet other embodiments, the conductivity of the elution buffer is at least 0.1 mS/cm lower or at least 0.2, 0.3, 0.4, 0.5, 0.6, 0.7, 0.8, 0.9, 1.0, 1.5, 2.0, 2.5, 3.0, 3.5, 4.0, 4.5, 5.0, or more lower than the conductivity of the loading buffer.

In another embodiment, the conductivity of the elution buffer is equal to or less than the conductivity of the wash buffer. In one embodiment, the conductivity of the elution buffer is at least 0.5 mS/cm lower than the conductivity of the wash buffer. In another embodiment, the conductivity of the elution buffer is at least 1.0 mS/cm lower than the conductivity of the wash buffer. In yet other embodiments, the conductivity of the elution buffer is at least 0.1 mS/cm lower or at least 0.2, 0.3, 0.4, 0.5, 0.6, 0.7, 0.8, 0.9, 1.0, 1.5, 2.0, 2.5, 3.0, 3.5, 4.0, 4.5, 5.0, or more lower than the conductivity of the wash buffer.

In one embodiment, the salt concentration of the first solution condition (i.e., the loading buffer) is between about 20 mM and about 500 mM. In another embodiment, the salt concentration is between about 20 mM and about 400 mM. In another embodiment, the salt concentration is between about 20 mM and about 300 mM. In yet another embodiment, the salt concentration is between about 20 mM and about 200 mM. In certain embodiments, the salt concentration of the first solution condition (i.e., the loading buffer) is about 20 mM, or about 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, or higher.

In one embodiment, the pH of the first solution condition (i.e., the loading buffer) is less than about 9.0. In another embodiment, the pH is less than about 8.5. In another embodiment, the pH is less than about 8.0. In another embodiment, the pH is less than about 7.5. In another embodiment, the pH is less than about 7.0. In another embodiment, the pH is less than about 6.5. In another embodiment, the pH is less than about 6.0. In yet other embodiments, the pH of the first solution condition (i.e., the loading buffer) is less than about 9.0, or less than about 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, or lower.

In one embodiment of the methods provided herein, the salt concentration of the third solution condition (i.e., the wash buffer) is between about 20 mM and about 500 mM. In another embodiment, the salt concentration is between about 20 mM and about 400 mM. In another embodiment, the salt concentration is between about 20 mM and about 300 mM. In yet another embodiment, the salt concentration is between about 20 mM and about 200 mM. In certain embodiments, the salt concentration of the third solution condition (i.e., the wash buffer) is about 20 mM, or about 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, or higher.

In one embodiment of the methods provided herein, the pH of the third solution condition (i.e., the wash buffer) is less than about 9.0. In another embodiment, the pH is less than about 8.5. In another embodiment, the pH is less than about 8.0. In another embodiment, the pH is less than about 7.5. In another embodiment, the pH is less than about 7.0. In another embodiment, the pH is less than about 6.5. In another embodiment, the pH is less than about 6.0. In yet other embodiments, the pH of the third solution condition (i.e., the wash buffer) is less than about 9.0, or less than about 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, or lower.

In one embodiment of the methods provided herein, the salt concentration of the second solution condition (i.e., the elution buffer) is between about 20 mM and about 500 mM. In another embodiment, the salt concentration is between about 20 mM and about 400 mM. In another embodiment, the salt concentration is between about 20 mM and about 300 mM. In yet another embodiment, the salt concentration is between about 20 mM and about 200 mM. In certain embodiments, the salt concentration of the second solution condition (i.e., the elution buffer) is at least 20 mM, or about 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, or higher.

In one embodiment of the methods provided herein, the pH of the second solution condition (i.e., the elution buffer) is higher than about 9.0. In another embodiment, the pH is higher than about 8.5. In another embodiment, the pH is higher than about 8.0. In another embodiment, the pH is higher than about 7.5. In another embodiment, the pH is higher than about 7.0. In another embodiment, the pH is higher than about 6.5. In another embodiment, the pH is higher than about 6.0. In yet other embodiments, the pH of the second solution condition (i.e., the elution buffer) is higher than about 9.0, or higher than about 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, or lower.

In one embodiment, the divalent cation present in the elution buffer is selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, and a combination thereof.

In one embodiment, the concentration of divalent cation present in the elution buffer is between about 0.1 mM and about 20 mM. In another embodiment, the concentration of divalent cation present in the elution buffer is between about 0.5 mM and about 10 mM. In another embodiment, the concentration of divalent cation present in the elution buffer is between about 1 mM and about 5 mM. In another embodiment, the concentration of divalent cation present in the elution buffer is between about 1 mM and about 3 mM. In another embodiment, the concentration of divalent cation present in the elution buffer is between about 1 mM and about 2 mM. In a specific embodiment, the concentration of the divalent cation present in the elution buffer is about 0.5 mM. In another embodiment, the concentration of divalent cation present in the elution buffer is about 1.0. In another embodiment, the concentration of divalent cation present in the elution buffer is about 2.0. In yet other embodiments, the concentration of divalent cation present in the elution buffer is about 0.1 mM or about 0.2 mM, 0.3 mM, 0.4 mM, 0.5 mM, 0.6 mM, 0.7 mM, 0.8 mM, 0.9 mM, 1.0 mM, 1.5 mM, 2.0 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 11 mM, 12 mM, 13 mM, 14 mM, 15 mM, 16 mM, 17 mM, 18 mM, 19 mM, 20 mM, 25 mM, 30 mM, or more.

In one embodiment, the anion exchange resin material has a positively charged group which is selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

In one embodiment, the anion exchange resin material has a positively charged group which is selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

In one embodiment, the anion exchange resin material carries a primary amine as ligand which is selected from the group, consisting of aminohexyl, benzamidine, lysine, and arginine.

In one embodiment, the divalent cation binding protein is a calcium binding protein. In one embodiment, the divalent cation binding protein is a protein found in blood. In one embodiment, the protein is a plasma-derived protein. In another embodiment, the protein found in blood is recombinantly expressed. In a specific embodiment, the divalent cation binding protein is selected from the group consisting of Factor IX, Factor VII, Annexin V, Factor X, Protein C, and an ADAMTS protease (e.g., ADAMTS13). In one embodiment, the calcium binding protein contains a GLA domain. In a specific embodiment, the GLA domain containing protein is selected from BGLAP; FX; FII; FVII; FIX; GAS6; MGP; PROC; PROS1; PROZ; PRRG1; PRRG2; PRRG3; and PRRG4.

In one embodiment, the divalent cation binding protein is a vitamin K-dependent protein. In one embodiment, the vitamin K-dependent protein is plasma-derived. In another embodiment, the vitamin K-dependent protein is recombinant. In a specific embodiment, the divalent cation binding protein is selected from the group, consisting of Factor IX, Factor VII, and Annexin V.

In one embodiment, the composition is formulated for pharmaceutical administration. Methods for formulating therapeutic proteins are well known in the art. Accordingly, in one embodiment, the present invention provides a pharmaceutical composition of a divalent cation binding protein prepared by a method comprising the steps of (a) loading an anion exchange resin material with the divalent cation binding protein in a loading buffer in the absence of divalent cations, and optionally washing the loaded anion exchange resin material with a washing buffer in the absence of divalent cations; (b) eluting the divalent cation binding protein with an eluant comprising at least one divalent cation to form an eluate containing the divalent cation binding protein; and (c) formulating the eluted divalent cation binding protein for pharmaceutical administration; wherein the eluant in step (b) has a pH higher than the pH of the washing buffer in step (a), or, in case no washing step is carried out, of the loading buffer in step (a).

In another embodiment, the present invention provides a pharmaceutical composition of a divalent cation binding protein prepared by a method comprising the steps of: (a) contacting a solution comprising the divalent cation binding protein with an anion exchange resin material under a first solution condition lacking available divalent cations at a first pH to bind the protein to the resin; (b) eluting the protein from the resin with a second solution condition comprising available divalent cations at a second pH; and (c) formulating the eluted protein for pharmaceutical administration, wherein the second pH is higher than the first pH.

In one embodiment, the method further comprises the step of washing the resin formed in step (a), prior to step (b), under a third solution condition lacking available divalent cations at a third pH, wherein the second pH is higher than the third pH.

In one embodiment, the present invention provides pharmaceutical compositions of a divalent cation binding protein prepared according to a method provided herein. In one embodiment, the divalent cation binding protein is a calcium binding protein. In one embodiment, the divalent cation binding protein is a protein found in blood. In one embodiment, the protein is a plasma-derived protein. In another embodiment, the protein found in blood is recombinantly expressed. In a specific embodiment, the divalent cation binding protein is selected from the group consisting of Factor IX, Factor VII, Annexin V, Factor X, Protein C, and an ADAMTS protease (e.g., ADAMTS13). In one embodiment, the calcium binding protein contains a GLA domain. In a specific embodiment, the GLA domain containing protein is selected from BGLAP; FX; FII; FVII; FIX; GAS6; MGP; PROC; PROS1; PROZ; PRRG1; PRRG2; PRRG3; and PRRG4. In one embodiment, the divalent cation binding protein is a vitamin K-dependent protein. In one embodiment, the vitamin K-dependent protein is plasma-derived. In another embodiment, the vitamin K-dependent protein is recombinant. In a specific embodiment, the divalent cation binding protein is selected from the group, consisting of Factor IX, Factor VII, and Annexin V.

The pharmaceutical compositions provided herein are prepared by according to a method provided herein. In one embodiment, the formulated composition will have been subjected to at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol.* 1991 (72 (pt 8)):2021-2024, both of which are herein expressly incorporated by reference in their entirety for all purposes), and low pH incubation at high temperatures (Kempf et al., *Transfusion* 1991 (31)-423-427 and Louie et al., *Biologicals* 1994 (22):13-19).

V. Kits

Further, in another aspect of the present invention, kits are provided comprising means for carrying out the method of the present invention. In particular, the present invention relates to a kit comprising an eluant comprising at least one divalent cation, suitable for eluting a divalent cation binding protein from an anion exchange resin material in a buffer, wherein the pH of the eluant is higher than the pH of the buffer. For example, the kit may contain a loading buffer and/or an eluant and/or a washing buffer and/or an additional washing buffer which are suitable for the purification of a divalent cation binding protein using an anion exchange resin material according to the present invention. In a preferred embodiment, the loading buffer, the washing buffers and/or the eluant are as defined above. Further, the kit of the present invention may contain a suitable anion exchange resin material.

Various modifications and variations of the described method and products of the invention will be apparent to those skilled in the art without departing from the scope and spirit of the invention. Although the invention has been described in connection with specific preferred embodiments, it should not be unduly limited to such embodiments.

VI. Examples

The following examples are provided as a guide for a person skilled in the art. The examples should not be construed as limiting the invention, the examples merely provide specific methodology useful in understanding and practicing an embodiment of the invention.

Example 1

Purification of rFIX on Q-Sepharose FF

A Q-Sepharose Fast Flow resin was activated with 2 column volumes (CV) of 2 M NaCl and equilibrated with 4 CV of an equilibration buffer (20 mM Tris, 2 mM EDTA, pH 7.4, conductivity approximately 2 mS/cm). Thereafter, a FIX containing filtered cell culture supernatant obtained from a genetically engineered CHO cell line supplemented with 3 mM EDTA was loaded onto the column at a linear flow rate of about 150 cm/h having a conductivity of about 13 to 15 mS/cm. The column was then washed with 2 CV of equilibration buffer followed by a second wash with 5 CV washing buffer (20 mM MES, 2 mM EDTA, 175 mM NaCl, pH 6.0) to remove the majority of protein impurities that do not bind onto the anion exchange resin material at pH 6.0. Before the elution, the conductivity in the column was again reduced by applying a 2 CV wash with equilibration buffer. Bound FIX was eluted with 5 CV of the eluant (20 mM Tris, 2 mM CaCl2, 180 mM NaCl, pH 8.0). The results in Table 1 show that by applying this procedure, the divalent cation binding protein product with a purity of 98% could be obtained with a single purification step by anion exchange chromatography out of the cell culture supernatant matrix.

TABLE 1

Purification of rFIX on Q-Sepharose FF

| | FIX Antigen µg/ml | CHO protein µg/ml | FIX purity % | CHO impurity level ng CHO/µg FIX Antigen |
|---|---|---|---|---|
| Load | 6.2 | 13.4 | 32 | 2161 |
| Eluate pool | 105.3 | 2.43 | 98 | 23.1 |

Example 2

Purification of FVII on Q-Sepharose FF

A Q-Sepharose Fast Flow resin was activated with 2 CV of 2 M NaCl and equilibrated with 5 CV of an equilibration buffer (20 mM Tris, 2 mM EDTA, pH 7.5, conductivity approximately 2 mS/cm). Thereafter, a FVII containing filtered cell culture supernatant obtained from a genetically engineered CHO cell line supplemented with 9 mM EDTA was loaded onto the column at a linear flow rate of about 46 cm/h having a conductivity of about 16 mS/cm. The column was then washed with 4 CV of equilibration buffer followed by a second wash with 5 CV washing buffer (20 mM MES, 2 mM EDTA, 170 mM NaCl, pH 6.0) to remove the majority of protein impurities that do not bind onto the anion exchange resin material at pH 6.0. Before the elution, the conductivity in the column was again reduced by applying a 2 CV wash with equilibration buffer. Bound FIX was eluted with 5 column volumes of the eluant (20 mM Tris, 2 mM CaCl2, 180 mM NaCl, pH 8.0). The results in Table 2 show that by applying this procedure the divalent cation binding product with a purity of 97% could be obtained with a single purification step by anion exchange chromatography out of the cell culture supernatant matrix.

TABLE 2

Purification of rFVII on Q-Sepharose FF

|  | FVII Antigen µg/ml | CHO protein µg/ml | FVII purity % | CHO impurity level ng CHO/µg FVII Antigen |
|---|---|---|---|---|
| Load | 7.4 | 26.3 | 22 | 3554 |
| Eluate pool | 13.0 | 0.43 | 97 | 30 |

Example 3

Purification of Human Annexin V on Q-Sepharose FF

A Q-Sepharose Fast Flow resin was activated with 4 CV of 2 M NaCl and equilibrated with 15 CV of an equilibration buffer (20 mM Tris, 2 mM EDTA, pH 7.5, conductivity approximately 2 mS/cm). Thereafter, an Annexin V protein preparation purified from human placenta was spiked with a protein stock solution obtained from a CHO cell line to generate a protein load with an Annexin purity of below 20%. The Annexin containing protein mixture was supplemented with 1 mM EDTA and loaded onto the column at a linear flow rate of about 23 cm/h having a conductivity of about 4 mS/cm. The column was then washed with 10 CV of equilibration buffer followed by a second wash with 10 CV washing buffer (20 mM MES, 2 mM EDTA, 155 mM NaCl, pH 6.0) to remove the majority of protein impurities that do not bind onto the anion exchange resin material at pH 6.0. Before the elution, the conductivity in the column was again reduced by applying a 10 CV wash with equilibration buffer. Bound Annexin was eluted with 30 CV of the eluant (20 mM Tris, 2 mM CaCl2, 150 mM NaCl, pH 8.0). The elution buffer had the same conductivity as the wash buffer. The resulting fractions were analyzed by SDS polyacrylamide gelelectrophoresis on a 12% gel under reducing conditions. The gels with the separated polypeptides stained for total protein (silver stain) and Annexin V (anti-Annexin Western blot) are depicted in FIG. 1. The results show that in the elution fractions A2 to A4 Annexin V is contained in a high purity compared to the protein mix that was loaded onto the column (fraction load). The data indicate that after a single purification step by anion exchange chromatography the divalent cation binding protein could be obtained in a high purity in the elution fractions.

Example 4

Purification of rFIX on Q-Sepharose FF

Various conditions for purifying FIX from host cell proteins (HCP) using Q-Sepharose Fast Flow were tested. In particular, the procedure included the following conditions:
Run 1: Load neutral pH, wash low pH 6.5, elution high pH 7.9, conductivity equal in wash and elution buffer.
Run 2: Load neutral pH, wash low pH 6.0, elution high pH 8.0, conductivity in wash buffer lower than in elution buffer.
Run 2.1: same as run 2, salt concentration in wash increased.

In all experiments a second wash was performed immediately before the elution with a buffer of low conductivity. In all experiments the conductivity of the elution buffer is higher than the loading buffer. The results are shown in Table 3.

TABLE 3

Purification of rFIX on Q-Sepharose FF

|  | Load | Wash 1 | Wash 2 | Elution | Comment | purity of eluate pool ng HCP/µg FDC | CHO reduction factor reduction of spec. impurity | µg load/µg eluate pool |
|---|---|---|---|---|---|---|---|---|
| run 1 | 20 mM Tris, approx. 150 mM NaCl, 2 mM EDTA, pH = 7.4 | 20 mM MES, 160 mM NaCl, 2 mM EDTA, pH = 6.5 | 20 mM Tris, pH = 7.4 | 20 mM Tris, 180 mM NaCl, 2 mM CaCl2, pH = 7.9 | Wash low pH, elution buffer high pH conductivity equal in wash and elution buffer | 21 | 56 | 175 |
| run 2 | 20 mM Tris, approx. 150 mM NaCl, 2 mM EDTA, pH = 7.4 | 20 mM MES, 165 mM NaCl, 2 mM EDTA, pH = 6.0 | 20 mM Tris, pH = 7.4 | 20 mM Tris, 180 mM NaCl, 2 mM CaCl2, pH = 8.0 | Wash low pH, elution buffer high pH conductivity in wash buffer lower than in elution buffer | 28 | 81 | 195 |
| run 2.1 | 20 mM Tris, approx. 150 mM NaCl, 2 mM EDTA, pH = 7.4 | 20 mM MES, 175 mM NaCl, 2 mM EDTA, | 20 mM Tris, pH = 7.4 | 20 mM Tris, 180 mM NaCl, 2 mM CaCl2, pH = 8.0 | Wash low pH, elution buffer high pH conductivity in wash buffer | 23 | 94 | 143 |

TABLE 3-continued

Purification of rFIX on Q-Sepharose FF

| | | | | | purity of eluate pool ng HCP/ μg FDC | CHO reduction factor | |
|---|---|---|---|---|---|---|---|
| Load | Wash 1 | Wash 2 | Elution | Comment | | reduction of spec. impurity | μg load/μg eluate pool |
| | pH = 6.0 | | | lower than in elution buffer | | | |

Example 5

Comparative Purification of rFIX on Q-Sepharose FF

In order to demonstrate the beneficial effects of the method of the present invention, two comparative chromatographic runs were performed. In particular, rFIX from a clarified CHO cell culture supernatant was purified on Q-Sepharose FF, wherein Run 1 was performed according to the method of the present invention, i.e., the pH of the eluant in step (b) had a pH higher than the pH of the washing buffer in step (a), and Run 2 was performed in the same manner but without any pH difference between loading/washing in step (a) and elution in step (b). The respective buffer condition are summarized in Table 4.

TABLE 4

Buffer conditions of two chromatographic rFIX purification runs

| | pH | | |
|---|---|---|---|
| | Run 1 | Run 2 | $Ca^{2+}$ |
| Loading | 6 | 7.6 | absent, 2 mM EDTA |
| Wash 1 | 6 | 7.6 | absent, 2 mM EDTA |
| Wash 2 | 7.6 | 7.6 | absent, 2 mM EDTA |
| Elution | 7.6 | 7.6 | present |

The fractions obtained were analyzed for rFIX activity yield, rFIX antigen yield, reduction factor of CHO host cell proteins (CHO HCP), and rFIX specific activity. The reduction factor of CHO HCP was calculated as the ratio of total CHO HCO loaded to CHO HCP found in the eluate. The respective data are summarized in Table 5.

TABLE 5

Results of two chromatographic rFIX purification runs

| | rFIX activiy yield [%] | rFIX antigen yield [%] | CHO HCP reduction factor | rFIX spec. activity [U/mg rFIX] |
|---|---|---|---|---|
| Run 1 | 88 | 33 | 239 | 266 |
| Run 2 | 95 | 36 | 112 | 134 |

These results indicate that the method of the present invention, in particular the pH change between load/wash and elution, can significantly improve reduction of contaminant host cell proteins and specific activity of the purified protein.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for the purification of a Factor IX (FIX) protein comprising the steps of:
   (a) loading an anion exchange resin material with the Factor IX (FIX) protein in a loading buffer, wherein the loading buffer contains a chelating agent and no free divalent cations;
   (b) washing the loaded anion exchange resin material prepared in step (a) with a wash buffer, wherein the wash buffer does not contain sufficient divalent cations to elute the Factor IX (FIX) protein,
   wherein the salt concentration of the wash buffer is between 165 mM and 175 mM,
   wherein the pH of the wash buffer is less than 6.5;
   (c) washing the loaded anion exchange resin material prepared in step (b) with a wash buffer, wherein the wash buffer does not contain sufficient divalent cations to elute the Factor IX (FIX) protein and wherein the pH of the wash buffer is about 7.3 to 7.5, and
   wherein there is no additional wash step after (b) and before (c); and
   (d) eluting the Factor IX (FIX) protein with an elution buffer comprising at least one divalent cation to form an eluate containing the Factor IX (FIX) protein;
   wherein the elution buffer has a pH at least 0.5 pH units higher than the pH of the loading buffer in step (a),
   wherein the elution buffer has a pH at least 1.5 pH units higher than the pH of the wash buffer in step (b),
   wherein the pH of the elution buffer is greater than or equal to 7.9,
   and wherein the FIX protein in the eluate has a purity with respect to host cell protein impurities of at least 98% w/w.

2. The method of claim 1, wherein the elution buffer in step (d) has a pH at least 2.0 pH units higher than the pH of the wash buffer in step (b).

3. The method according to claim 1, wherein the wash buffer of step (b) has a conductivity that is equal or lower than the conductivity of the elution buffer in step (d).

4. The method according to claim 1, wherein the at least one divalent cation in step (d) is selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, and a combination thereof.

5. The method according to claim 1, wherein the anion exchange resin material has a positively charged group which is selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

6. The method according to claim 1, wherein the anion exchange resin material carries a primary amine as ligand which is selected from the group, consisting of aminohexyl, benzamidine, lysine, and arginine.

7. The method of claim 1, wherein the wash buffer in step (b) and the wash buffer in step (c) do not contain divalent cations.

8. The method of claim 1, wherein the FIX protein in the eluate has a purity with respect to host cell protein impurities of at least 99% w/w.

* * * * *